United States Patent [19]

Stanford et al.

[11] Patent Number: 5,554,138
[45] Date of Patent: Sep. 10, 1996

[54] THORACIC CATHETER WITH ELONGATED PULLING LEAD

[75] Inventors: Charles G. Stanford, West Bend; Michael J. Brown, Brookfield, both of Wis.

[73] Assignee: Medovations, Germantown, Wis.

[21] Appl. No.: 353,678

[22] Filed: Dec. 12, 1994

[51] Int. Cl.$^6$ ................................................ A61M 25/00
[52] U.S. Cl. .................... 604/280; 604/264; 604/272; 128/770
[58] Field of Search ................... 128/760, 768, 128/770, 772; 604/264, 280, 27, 29, 51, 93, 270, 272, 276, 317, 327, 96, 44

[56] References Cited

U.S. PATENT DOCUMENTS

| | | | |
|---|---|---|---|
| 2,097,039 | 10/1937 | Peterson | 604/266 |
| 2,492,384 | 12/1949 | Kaslow . | |
| 2,857,915 | 10/1958 | Sheridan | 604/280 |
| 3,190,290 | 6/1963 | Alley et al. . | |
| 3,295,527 | 1/1967 | Alley et al. | 604/280 |
| 3,384,089 | 5/1968 | Shriner | 604/280 |
| 3,459,189 | 8/1969 | Alley et al. . | |
| 3,589,368 | 6/1971 | Jackson et al. . | |
| 3,595,241 | 7/1971 | Sheridan | 604/280 |
| 3,633,585 | 1/1972 | McDonald, Jr. . | |
| 4,617,019 | 10/1986 | Fecht et al. | 604/280 |
| 4,762,519 | 8/1988 | Frimberger . | |
| 4,769,016 | 9/1988 | Labianca . | |
| 4,834,723 | 5/1989 | Sheridan et al. . | |
| 4,842,589 | 6/1989 | Fecht et al. | 604/280 |
| 4,883,474 | 11/1989 | Sheridan et al. | 604/272 |
| 4,955,859 | 9/1990 | Zilber . | |
| 4,991,602 | 2/1991 | Amplatz et al. . | |
| 5,152,756 | 10/1992 | Quinn et al. . | |
| 5,176,664 | 1/1993 | Weisman . | |
| 5,275,611 | 1/1994 | Behl . | |
| 5,306,240 | 4/1994 | Berry | 604/51 |
| 5,320,611 | 6/1994 | Bonutti et al. . | |
| 5,336,177 | 8/1994 | Marcus | 604/264 |

*Primary Examiner*—Corrine M. McDermott
*Assistant Examiner*—N. Kent Gring
*Attorney, Agent, or Firm*—Andrus Sceales Starke & Sawall

[57] ABSTRACT

The thoracic catheter has an elongated, integrally formed lead designed to be pulled by the surgeon without the use of a clamp. The lead has sufficient length to allow it to be readily held within the surgeon's hand, or even wrapped around the hand. A tip at the proximal end of the lead is used to guide the lead through the chest wall. In the alternative, the tip may have a trocar that is used to make the secondary incision in the chest wall for the placement of the catheter.

11 Claims, 2 Drawing Sheets

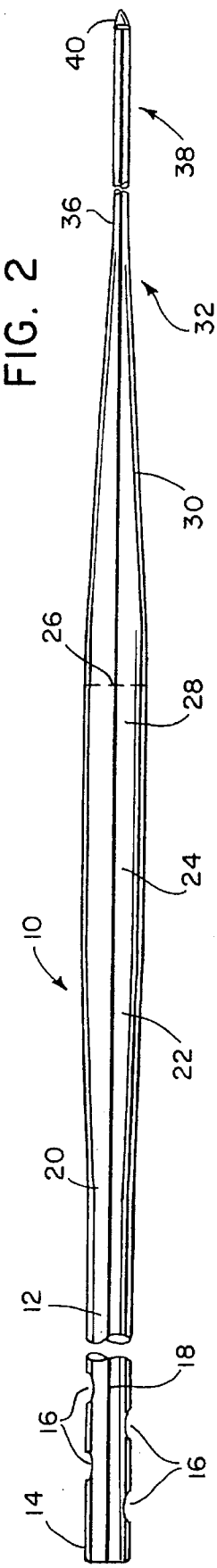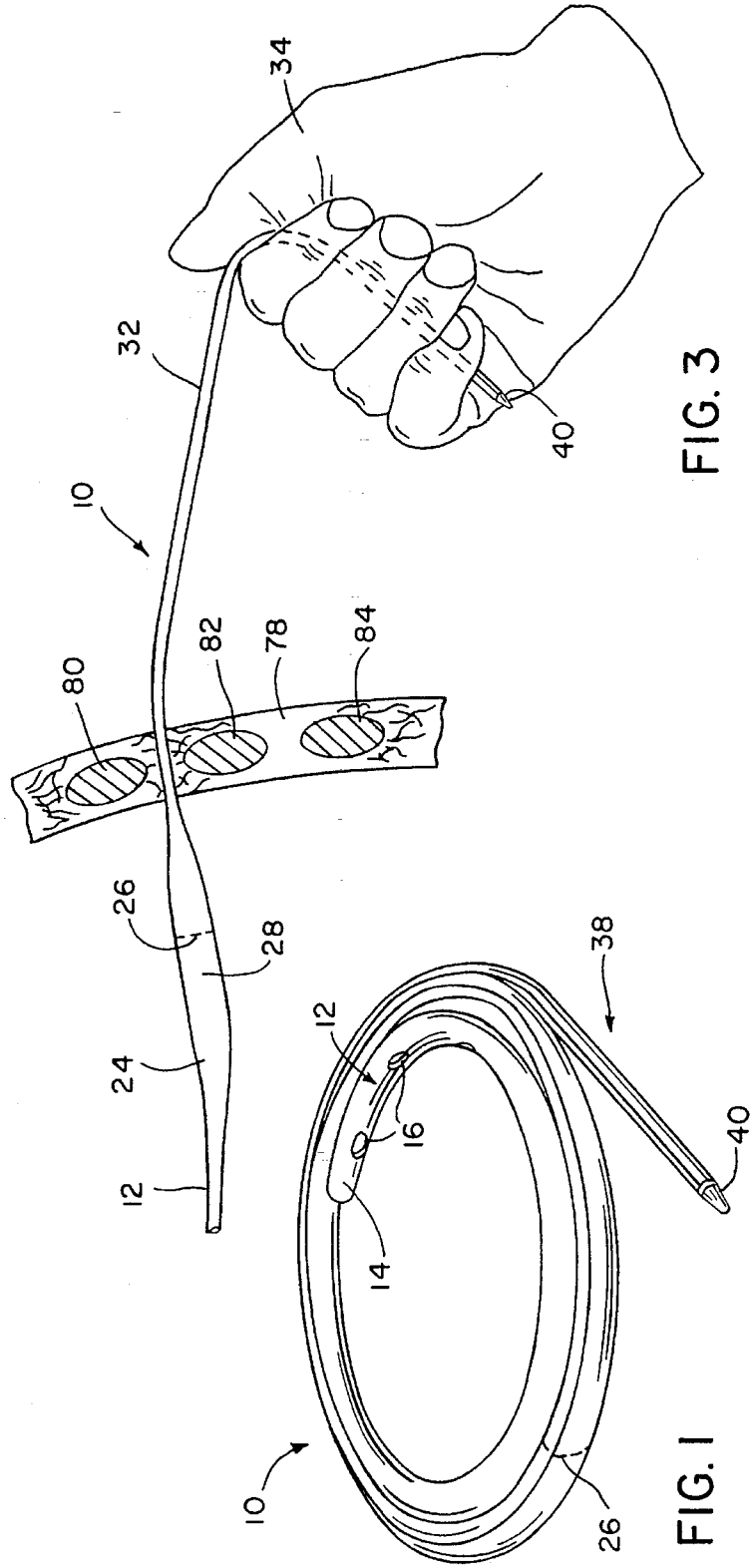

THORACIC CATHETER WITH ELONGATED PULLING LEAD

BACKGROUND OF THE INVENTION

This invention relates to thoracic catheters of the type used for postsurgical drainage purposes to remove air and/or body fluids from the chest or other body cavities of patients.

After open chest surgery, it is generally necessary to drain fluids and/or air created by the patient's body as a result of the surgery. Thoracic catheters are used for this purpose. To drain the air and/or body fluids, an additional or secondary incision is made between the patient's ribs from the outside of the chest. A hemostat or clamp is placed through the secondary incision. The hemostat or clamp then punctures the pleura, if the pleura had not already been cut during the making of the secondary incision. The thoracic catheter is then placed through the open chest cavity and is grasped on its proximal end by the hemostat. The hemostat is then used to pull the catheter through the chest wall and into position to achieve proper chest drainage. It may be necessary to then cut off the proximal tip of the catheter, depending on the type of catheter being used, to create a funnel end that is connected to a negative pressure-generating apparatus.

There are several disadvantages of the typical prior art thoracic catheter discussed above. A first disadvantage is that a clamp or hemostat must be used to pull the catheter through the secondary incision and, in most cases, to also rupture the pleura. The hemostat or clamp may slip and puncture a lung or tear the end of the catheter.

A second disadvantage of prior art thoracic catheters is that a relatively large secondary incision is required to enable the catheter to be pulled through the secondary incision. The large secondary incision is needed to permit the clamp or hemostat to enter the secondary incision for pulling of the catheter. The large incision results in more tissue damage and requires greater time to heal.

A third disadvantage of such prior art catheters is that the large secondary incision may make proper sealing between the secondary incision opening and the catheter difficult to achieve. A poor seal may allow infection-causing bacteria to enter the space between the secondary incision and the catheter.

A fourth disadvantage of such prior art catheters is that such catheters are difficult to use with patients having thicker chest walls. On such patients, it is difficult to maneuver and grasp the proximal end of the catheter with the hemostat or clamp to pull the catheter through the chest wall.

A fifth disadvantage of these typical prior art catheters also results from the large secondary incision. The large secondary incision does not provide support to the catheter to keep the catheter in place along with the sutures that may be used to seal the space between the catheter and the tissue.

SUMMARY OF THE INVENTION

A thoracic catheter is disclosed that may be pulled through a cavity wall without the use of any clamps or similar implements, and that may, in one embodiment, include a trocar used to create the secondary incision for the catheter.

The thoracic catheter includes a body made of a flexible plastic material with a lumen extending the length of the body. The body has a distal end having a first diameter, and a proximal end. A central tubular section having a diameter larger than the body has a distal end integrally connected to the proximal end of the body, and a proximal end integrally connected to an elongated pulling lead made of a flexible plastic material. The central tubular section has a mark indicating where the tubular section should be cut to form a funnel end.

The elongated pulling lead is made of a flexible plastic material and has a diameter that is substantially less than the diameter of the body's distal end. The elongated pulling lead is between about 2 to 12 inches long so that it may be grasped by the surgeon's hand or wrapped around the hand and pulled without the use of a clamp.

The invention also includes a tip connected to the proximal end of the pulling lead. The tip may have a number of different configurations, including a rounded end, a conical radiused end, a rigid insert, a malleable insert, or even a trocar that is used to make the secondary incision.

It is a feature and advantage of the present invention to provide a thoracic catheter that does not require a clamp or other implement to pull the catheter through the secondary incision.

It is another feature and advantage of the present invention to provide a thoracic catheter having an elongated lead that may be gripped by the surgeon's hand.

It is yet another feature and advantage of the present invention to provide a thoracic catheter having a trocar that may be used to make the secondary incision for the catheter.

These and other features and advantages of the present invention will be apparent to those skilled in the art from the following detailed description of the preferred embodiments and the drawings, in which:

BRIEF DESCRIPTION OF THE DRAWINGS

FIG. 1 depicts a thoracic catheter according to the present invention having a trocar inserted in the tip end.

FIG. 2 is a side view of the catheter depicted in FIG. 1.

FIG. 3 depicts a thoracic catheter according to the present invention being pulled through a chest cavity wall.

DETAILED DESCRIPTION OF THE PREFERRED EMBODIMENT

Figure 4:
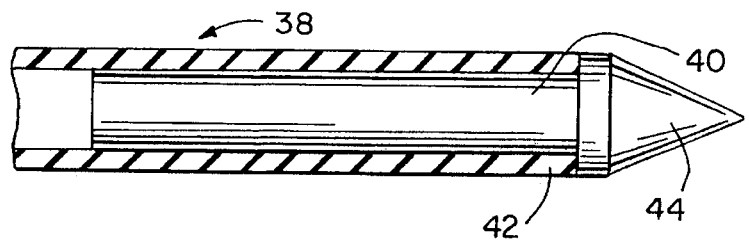
FIGS. 4 through 9 depict different tips that may be used in the catheter of the present invention.

Referring to FIGS. 1 through 3, a thoracic catheter 10 according to the present invention has a body 12 made of a flexible material such as plasticized polyvinyl chloride, silicon, polyurethane, or hytrel. Body portion 12 has a distal end 14 that includes a plurality of apertures 16 into which air and/or the patient's body fluids drain in response to the application of a negative pressure to a funnel end of the catheter.

Body portion 12 has a lumen extending therethrough, and a radiologically opaque line 18 that extends the length of the catheter.

A proximal end 20 of body 12 is integrally connected to a distal end 22 of a central tubular section 24. Tubular section 24 has a lumen therethrough, and an inside diameter and an outside diameter that are substantially larger than the respective inside and outside diameters of body 12. The outside diameter of tubular section 24 is approximately 25 to 70 percent larger than the outside diameter of body 12. A mark or other indicator 26 is provided on tubular section 24 to indicate where tubular section 24 should be cut to create funnel end 28 of tubular section 24. After the cut has been made, funnel end 28 is interconnected with a negative pressure producing apparatus.

Integrally connected with the proximal, funnel end 28 of central tubular section 24 is a distal end 30 of an elongated flexible lead 32. Lead 32 has inside and outside diameters that are substantially less than the respective inside and outside diameters of distal end 14 of body portion 12 and of central tubular section 24. The outside diameter of lead 32 is approximately 30 to 70 percent the size of the outside diameter of distal end 14.

Lead 32 must have sufficient length to be readily gripped and held in a surgeon's hand 34 (FIG. 3). Lead 32 should have a length of at least 2 inches and may have a length as long as 12 inches beyond proximal end 30 of tubular section 24. If lead 32 is longer than several inches, it may be wrapped around the fingers of the surgeon's hand 34 for ease in pulling the catheter through the secondary incision in the chest wall.

Also, lead 32 must have sufficient strength to be readily pulled without breaking or significant stretching. Although lead 32 could be longer than 12 inches, the strength of the lead may thereby be reduced since the catheter and the lead are preferably made by drawing a single plasticized tube.

Lead 32 has a proximal end 36 to which is attached a tip 38. The embodiment depicted in FIGS. 1 through 4 includes a trocar 40 that has been inserted into open end 42 of tip 38. Trocar 40 has a very sharp conical end 44, and is preferably made from anodized aluminum or surgical steel. It is desirable to use a trocar in tip 38 in some cases to allow the trocar to pierce the chest cavity wall or other tissue, without the need to first make a secondary incision for the catheter in the chest cavity wall.

In addition to trocar 40, many other types of tips may be used in the present invention. Some examples of different types of tips are depicted in FIGS. 5 through 9.

Figure 5:
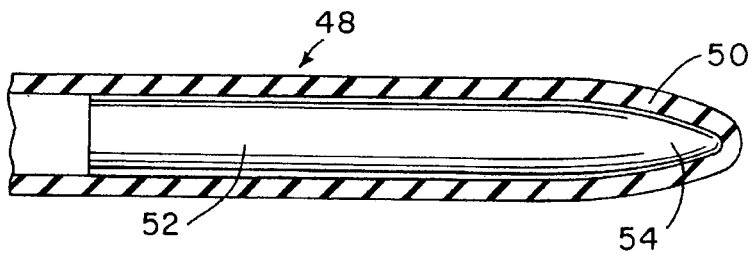

FIG. 5 depicts another catheter tip 48 having a closed, radiused end 50. Inserted within tip 48 is a rigid member 52 having a radiused end 54 that corresponds in shape to radiused end 50 of tip 48.

Figure 6:
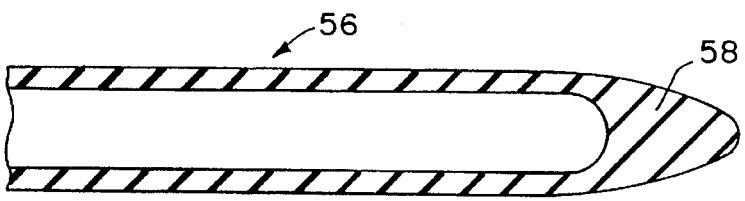

FIG. 6 depicts yet another catheter tip 56 having a closed, radiused end 58, with no insert within the tip.

Figure 7:
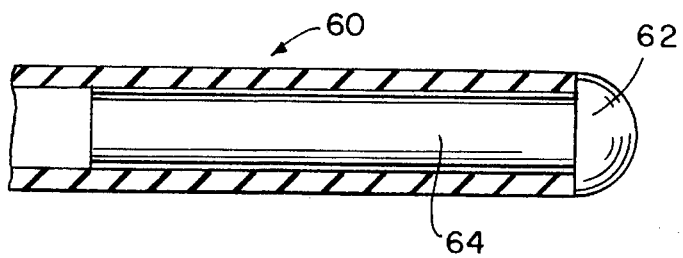

In the embodiment depicted in FIG. 7, tip 60 has a closed, rounded end 62 and a rigid member 64 disposed in tip 60.

Figure 8:
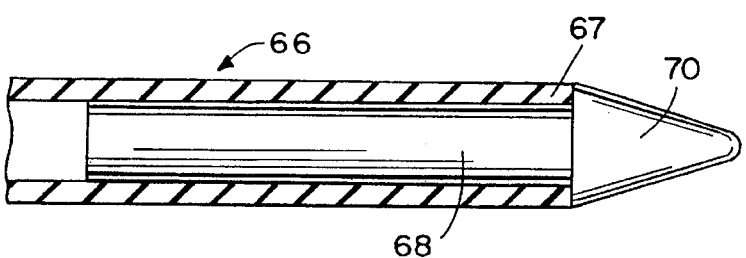

Tip 66 in FIG. 8 has an open end 67, and a rigid member 68 disposed within open end 67. Rigid member 68 has a radiused tip 70 extending from the open tip end.

Figure 9:
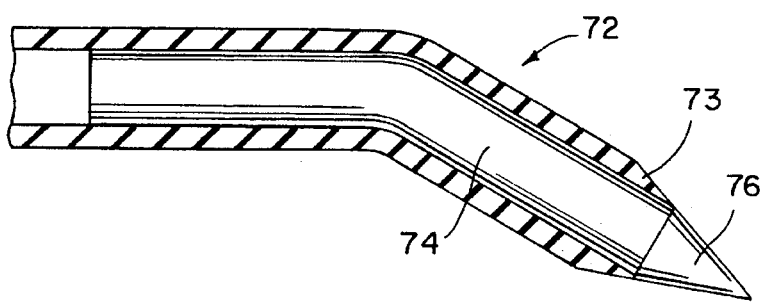

Finally, FIG. 9 depicts a tip 72 having an open end 73, into which a semirigid, malleable member 74 is inserted. Member 74 is shapeable, and is preferably made from a thermoset or thermoplastic, such as polyethylene or polypropylene. Member 74 may have a pointed end 76 as depicted in FIG. 9, or it may have a rounded end similar to end 62 in FIG. 7, or a radiused end similar to end 70 in FIG. 8. Indeed, any of the rigid members depicted and described in connection with FIGS. 5, 7 or 8 may be made out of a shapeable, semirigid material. The purpose of having a shapeable insert is to allow the tip end to be bent so that it may more readily be placed through the secondary incision in the chest wall.

Each of the rigid plastic members inserted into the catheters of FIGS. 5, 7 and 8 is made from rigid polyvinyl chloride, nylon, polycarbonate, or ABS plastic.

The use of the catheter according to the present invention will be described in connection with FIG. 3. When a surgery is being performed in the chest cavity or otherwise, a primary incision is made. After the surgery has been completed, a thoracic catheter is placed to permit drainage of air and/or body fluids out of the chest cavity. FIG. 3 depicts a chest wall 78 having a plurality of spaced ribs 80, 82 and 84. Assuming that the surgery is performed in the chest cavity, thoracic catheter 10 is drawn through the tissue between ribs 80 and 82.

If catheter 10 has a trocar end as depicted in FIGS. 1 through 4, the sharp trocar may be used to puncture the tissue between ribs 80 and 82 so that the catheter is placed without an incision being made by a scalpel or the like. If catheter 10 does not have a trocar end, a secondary incision is first made in tissue 78, and the tip of the catheter is inserted through the secondary incision.

In any event, once the tip of catheter 10 has been moved through the tissue between the ribs, lead 32 is grasped in the palm of the surgeon's hand 34, and may be wrapped around the hand. The surgeon then pulls lead 32 until mark 26 in central section 24 has passed between the ribs and is now the outside chest cavity wall. Central tubular section 24 is then cut at mark 26 to create funnel connection end 28, to which a negative pressure-producing apparatus is connected. Air and/or body fluids are then drawn through apertures 16, through catheter body 12, and out funnel end 28.

While several embodiments of the present invention have been shown and described, alternate embodiments will be apparent to those skilled in the art and are within the intended scope of the present invention. Therefore, the invention is to be limited only by the following claims.

We claim:

1. A thoracic catheter suitable for being placed in the open thoracic cavity of a patient following surgery to receive fluids found in the cavity, said catheter being capable of being drawn by a user in a facile manner through an opening in the thoracic wall from inside the thorax to outside the thorax to permit removal of the fluids from the cavity through the catheter, said catheter comprising:

an elongated body suitable for being placed in the thoracic cavity of the patient, said body having a lumen extending along its length, at least one opening extending through said body and to said lumen so that fluids found in the thoracic cavity may be received in said lumen, said body having a distal end portion with a first diameter, and said body having a proximal end;

a tubular section having a lumen extending along its length and being in fluid communication with the lumen of said body for receiving fluids, said tubular section having a second diameter greater than said first diameter, said tubular section having a distal end portion connected to, and merging smoothly with, said proximal end of said body, said tubular section having a proximal end, said tubular section being severable intermediate its distal end portion and proximal end to create a discharge port for the thoracic catheter;

a hollow elongated pulling lead having a third diameter less than said first diameter, said elongated pulling lead having a distal end portion connected to, and merging smoothly with, said proximal end of said tubular section, said elongated pulling lead having a proximal end;

said body, tubular section, and elongated pulling lead being integrally formed of a single piece of flexible plastic material; and a tip member connected to the proximal end of said pulling lead so that a portion of said elongated pulling lead exists between said tubular section and said tip member having a flexibility and length sufficient to enable the elongated pulling lead to be bent and grasped under the fingers of the user across the width of the palm:

said tip member and elongated pulling lead being insertable through the opening in the thoracic wall from inside to outside the thorax, said elongated pulling lead being bent and grasped under the fingers of the user across the width of the palm to facilitate drawing the tubular section of the thoracic catheter through the opening and beyond the point at which said tubular section is severable to form the discharge port.

2. The thoracic catheter of claim 1, wherein said elongated pulling lead has a length of 2 to 12 inches.

3. The thoracic catheter of claim 1, wherein said third diameter is 30 to 70 percent the size of said first diameter.

4. The thoracic catheter of claim 1, wherein said tip member comprises a rigid member.

5. The thoracic catheter to claim 4, wherein said rigid member is disposed within said proximal end of said elongated pulling lead.

6. The thoracic catheter of claim 4, wherein said rigid member is a trocar affixed to said proximal end of said elongated pulling lead.

7. The thoracic catheter of claim 1, wherein said tip member comprises a malleable member disposed within said proximal end of said elongated pulling lead.

8. The thoracic catheter of claim 1, wherein said tip member includes a rounded proximal end.

9. The thoracic catheter of claim 1, wherein said tubular section has a second diameter that is 25 to 75 percent larger than said first diameter of said body distal end portion.

10. The thoracic catheter of claim 1, further comprising:

an indicator, disposed on said tubular section, that indicates where said tubular section should be severed to create said discharge port.

11. The thoracic catheter of claim 1 wherein said elongated pulling lead has a flexibility and length sufficient to enable the elongated pulling lead to be wrapped around the hand of the user.

* * * * *